US007029497B2

(12) United States Patent
Zhang et al.

(10) Patent No.: US 7,029,497 B2
(45) Date of Patent: Apr. 18, 2006

(54) ACCOMMODATIVE INTRAOCULAR LENS

(75) Inventors: Xiaoxiao Zhang, Fort Worth, TX (US); Yin Yang, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 288 days.

(21) Appl. No.: 10/442,771

(22) Filed: May 21, 2003

(65) Prior Publication Data

US 2004/0236423 A1 Nov. 25, 2004

(51) Int. Cl.
*A61F 2/16* (2006.01)

(52) U.S. Cl. ...................................... 623/6.4; 623/6.37

(58) Field of Classification Search ................. 623/6.4, 623/6.42, 6.37

See application file for complete search history.

(56) References Cited

U.S. PATENT DOCUMENTS

| | | | | |
|---|---|---|---|---|
| 5,275,623 | A | 1/1994 | Sarfarazi | |
| 5,366,501 | A * | 11/1994 | Langerman | 623/6.42 |
| 5,476,514 | A | 12/1995 | Cumming | |
| 5,496,366 | A | 3/1996 | Cumming | |
| 5,674,282 | A | 10/1997 | Cumming | |
| 6,197,059 | B1 | 3/2001 | Cumming | |
| 6,241,777 | B1 | 6/2001 | Kellan | |
| 6,261,321 | B1 | 7/2001 | Kellan | |
| 6,302,911 | B1 | 10/2001 | Hanna | |
| 6,695,881 | B1 * | 2/2004 | Peng et al. | 623/6.34 |
| 6,818,158 | B1 | 11/2004 | Pham et al. | |
| 2002/0107568 | A1 | 8/2002 | Zadno-Azizi et al. | |
| 2004/0039446 | A1 | 2/2004 | McNicholas | |
| 2004/0111151 | A1 | 6/2004 | Paul et al. | |
| 2004/0127984 | A1 | 7/2004 | Paul et al. | |

FOREIGN PATENT DOCUMENTS

| | | |
|---|---|---|
| WO | WO 91/15166 | * 10/1991 |
| WO | WO 01/34067 | 11/1999 |
| WO | WO 00/66037 | 11/2000 |
| WO | WO 03/059196 | 7/2003 |
| WO | WO 03/059208 | 7/2003 |

OTHER PUBLICATIONS

“A dual optic accommodating foldable intraocular lens” British Journal of Ophthalmology 2003;87:1083-1085.

* cited by examiner

*Primary Examiner*—David H. Willse
(74) *Attorney, Agent, or Firm*—Jeffrey S. Schira

(57) ABSTRACT

A single optic accommodative lens. The lens includes a non-circular ring with radial dimensions that are different in at least two meridians. The radial dimension of vertical meridian of the lens approximates the natural diameter of the capsular bag. The optic of the lens is connected to the ring at the vertical meridian by a pair of haptics.

6 Claims, 2 Drawing Sheets

ACCOMMODATIVE INTRAOCULAR LENS

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the JOL was a monofocal lens, requiring that the patient use a pair of spectacles or contact lenses for near vision. Advanced Medical Optics has been selling a bifocal IOL, the Array lens, for several years, but due to quality of issues, this lens has not been widely accepted.

Several designs for accommodative lOLs are being studied. For example, several designs manufactured by C&C Vision are currently undergoing clinical trials. See U.S. Patent Nos. 6,197,059, 5,674,282, 5,496,366 and 5,476,514 (Cumming), the entire contents of which being incorporated herein by reference. The lens described in these patents is a single optic lens having flexible haptics that allows the optic to move forward and backward in reaction to movement of the ciliary muscle. Similar designs are described in U.S. Pat. No. 6,302,911 B1 (Hanna) U.S. Pat. No. 6,261,321 B1 and U.S. Pat. No. 6,241,777 B1 (both to Kellan), the entire contents of which being incorporated herein by reference. The amount of movement of the optic in these single-lens systems, however, may be insufficient to allow for a useful range of accommodation. In addition, as described in U.S.

Pat. Nos. 6,197,059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not inherently resistive to the formation of posterior capsule opacification ("PCO").

The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1, the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system. In addition, none of these lens designs have addressed the problem with PCO noted above.

Therefore, a need continues to exist for a safe and stable accommodative intraocular lens that provides accommodation over a broad and useful range.

BRIEF SUMMARY OF THE INVENTION

The present invention improves upon the prior art by providing a single optic accommodative lens. The lens includes a non-circular ring with radial dimensions that are different in at least two meridians. The radial dimension of vertical meridian of the lens approximates the natural diameter of the capsular bag. The optic of the lens is connected to the ring at the vertical meridian by a pair of haptics. The radial dimension of horizontal meridian of the lens is slightly larger than the natural diameter of the capsular bag.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible accommodative lens.

These and other advantages and objectives of the present invention will become apparent from the detailed description and claims that follow.

DETAILED DESCRIPTION OF THE INVENTION

Figure 2:
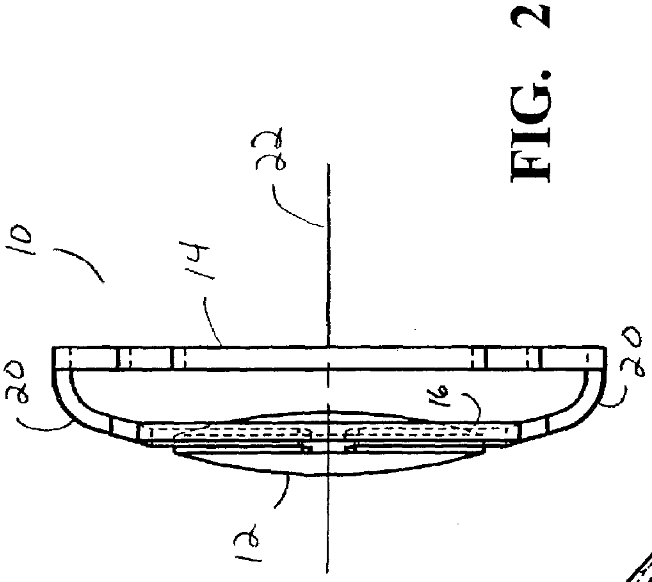
FIG. 2 is an enlarged side elevational view of a first embodiment of the lens of the present invention.
Figure 3:
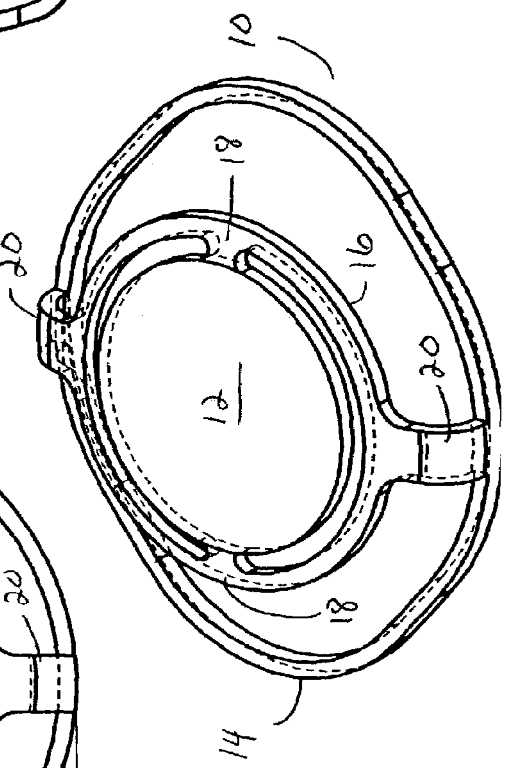
FIG. 3 is an enlarged perspective view of a first embodiment of the lens of the present invention.
Figure 1:
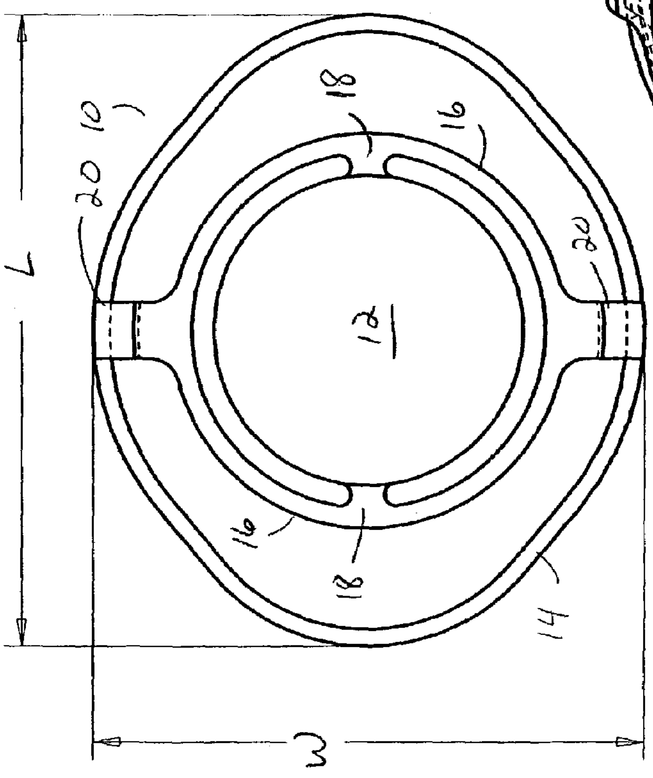
FIG. 1 is an enlarged top plan view of a first embodiment of the lens of the present invention.
Figure 5:
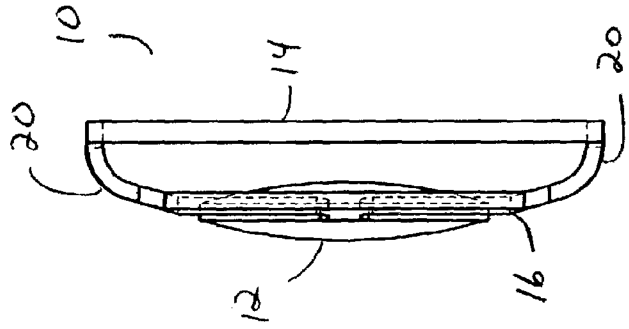
FIG. 5 is an enlarged side elevational view of a second embodiment of the lens of the present invention.
Figure 4:
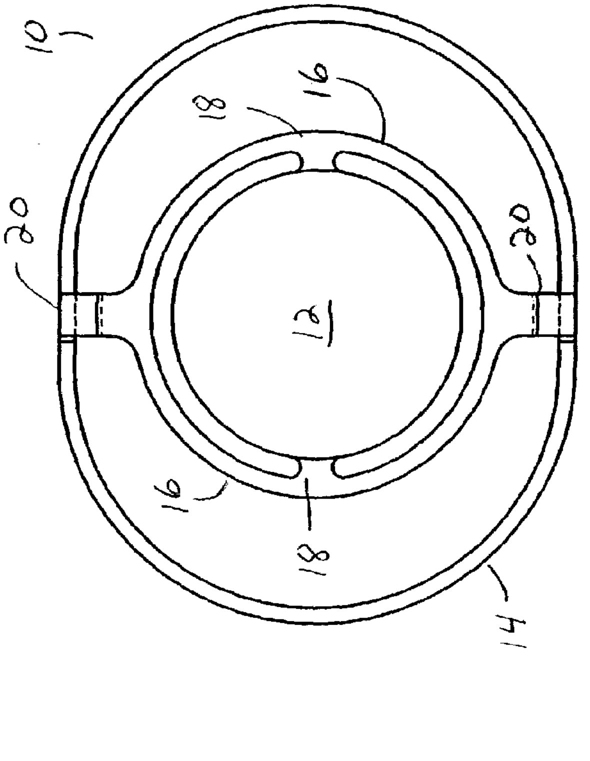
FIG. 4 is an enlarged top plan view of a second embodiment of the lens of the present invention.
Figure 6:
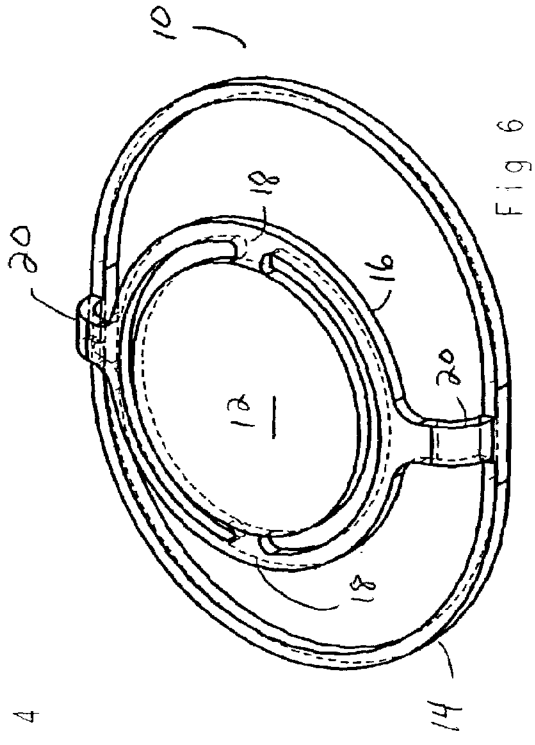
FIG. 6 is an enlarged perspective view of a second embodiment of the lens of the present invention.

As best seen in FIG. 1, lens 10 of the present invention generally consists of optic 12 and encircling ring 14. Ring 14 preferably has a length L along the horizontal meridian that is larger than width W along the vertical meridian. L preferably is between 9 millimeters and 13 millimeters, and W preferably is between 6 millimeters and 10 millimeters. Ring 14 may have a slightly scalloped shape, as illustrated in FIG. 1–3, or may be elliptical or oval, as illustrated in FIGS. 4–6. Optic 12 preferably is connected to flexible band 16 through hinges 18 and band 16 preferably is connected to ring 14 by haptics 20. Lens 10 preferably is made as a single piece from a soft, foldable material that is inherently resistive to the formation of PCO, such as a soft acrylic. Lens 10 may contain any suitable additive or chromophore for blocking ultraviolet and/or blue wavelengths of light. Optic 12 may be monofocal, multifocal, toric or of any other suitable optic design.

When implanted, the horizonal meridian of the capsular bag is stretched outward by length L of ring 14, thereby relaxing the zonules and causing the capsular bag to assume the slightly oval shape of ring 14. This "ovaling" of the capsular bag along the horizontal meridian is limited by tension in the zonules along the vertical meridian, which do not allow the capsular bag along the vertical meridian to constrict narrower than the normal diameter of the capsular bag. This constriction limitation prevents forward movement of optic 12 along the visual axis. During accommodation, the zonules located along the vertical meridian of the capsule bag relax, allowing the capsule bag to constrict ring 14 along the vertical meridian (decreasing width W) while the length L of ring 14 remains relatively unchanged, resulting in a more pronounced ovaling of the capsular bag. This constriction of ring 14 the vertical meridian is transferred to band 16 through haptics 20 so that band 16 is pulled posteriorly, flexing hinges 18. The flexing of hinges 18 causes optic 12 to be pushed anteriorly along visual axis 22.

This description is given for purposes of illustration and explanation. It will be apparent to those skilled in the relevant art that changes and modifications may be made to the invention described above without departing from its scope or spirit.

We claim:

1. An intraocular lens, comprising:

a) an optic;

b) a band surrounding the optic and attached to the optic by a plurality of hinges; and c) a ring surrounding the band and attached to the band by a plurality of haptics, the ring being generally elliptical in shape in an unstressed state, having a dimension L in a horizontal meridian greater than a dimension W in a vertical meridian.

2. The lens of claim 1 wherein the optic comprises a soft acrylic material.

3. An intraocular lens, comprising:

a) an optic;

b) a band surrounding the optic and attached to the optic by a plurality of hinges; and c) a ring surrounding the band and attached to the band by a plurality of haptics, the ring being generally oval in shape in an unstressed state, having a dimension L in a horizontal meridian greater than a dimension W in a vertical meridian.

4. The lens of claim 3 wherein the optic comprises a soft acrylic material.

5. An intraocular lens, comprising:

a) an optic;

b) a band surrounding the optic and attached to the optic by a plurality of hinges; and c) a ring surrounding the band and attached to the band by a plurality of haptics, the ring having a generally scalloped shape in an unstressed state, having a dimension L in a horizontal meridian greater than a dimension W in a vertical meridian.

6. The lens of claim 5 wherein the optic comprises a soft acrylic material.

* * * * *